United States Patent [19]
Cragoe, Jr. et al.

[11] 3,987,091

[45] Oct. 19, 1976

[54] 11,12-SECOPROSTAGLANDINS

[75] Inventors: Edward J. Cragoe, Jr., Lansdale; James H. Jones, Blue Bell, both of Pa.

[73] Assignee: Merck & Co., Inc., Rahway, N.J.

[22] Filed: June 4, 1975

[21] Appl. No.: 583,818

Related U.S. Application Data

[63] Continuation-in-part of Ser. No. 350,446, April 12, 1973, abandoned.

[52] U.S. Cl. .......................... 260/490; 260/247.2 A; 424/312; 424/316; 260/268 R; 424/318; 424/319; 260/284; 260/286 R; 260/293.86; 260/326 E; 260/326.5 L; 260/326.8; 260/326.85; 260/345.7; 260/345.8; 260/345.9; 260/404; 260/429.9; 260/439 R; 260/448 R; 260/456 A; 260/472; 260/482 R; 260/484 A; 260/484 R; 260/491; 260/501.11; 260/534 M; 260/561 A; 424/248; 424/250; 424/259; 424/262; 424/267; 424/274; 424/287; 424/289; 424/295; 424/311

[51] Int. Cl.² ................ C07C 103/48; C07C 103/66

[58] Field of Search ........... 260/482 R, 490, 534 M, 260/404, 501.11, 429.9, 439 R, 448 R, 211 R, 247.2 A, 268 R, 326.8, 293.86, 326.5 L, 326.85

[56] References Cited

OTHER PUBLICATIONS

Chem. Abstracts, 47:12360b.
Chem. Abstracts, 74:111185m.

*Primary Examiner*—Vivian Garner
*Attorney, Agent, or Firm*—Thomas E. Arther; Harry E. Westlake, Jr.; Rudolph J. Anderson, Jr.

[57] ABSTRACT

This invention relates to 8-aza-11,12-secoprostaglandins and processes for their manufacture. These compounds have prostaglandin-like biological activity and are particularly useful as renal vasodilators.

20 Claims, No Drawings

11,12-SECOPROSTAGLANDINS

RELATIONSHIP TO OTHER APPLICATIONS

This application is a continuation-in-part of copending U.S. patent application Ser. No. 350,446, filed April 12, 1973, now abandoned.

SUMMARY OF THE INVENTION

This invention relates to novel 8-aza-11,12-secoprostaglandins. These compounds can be represented by the following structural formula:

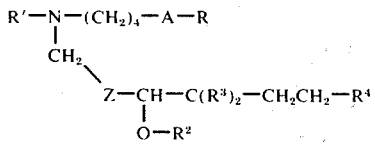

wherein R is selected from the group consisting of carboxy and a carboxy salt being formed from a pharmaceutically acceptable cation, such as metal cations derived from alkali metals, alkaline earth metals and amines such as ammonia, primary and secondary amines, and quaternary ammonium hydroxides. Especially preferred metal cations are those derived from alkali metals, e.g., sodium,, potassium, lithium,, and the like, and alkaline earth metals, e.g., calcium, magnesium, and the like, and other metals, i.e., aluminum, iron, and zinc.

Pharmaceutically acceptable cations derived from primary, secondary, or tertiary amines, or quaternary ammonium hydroxides are methylamine, dimethylamine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)-aminomethane, N-methylglucamine, N-methylglucosamine, ephedrine, procaine, tetramethylammonium hydroxide, tetraethylammonium hydroxide, benzyltrimethylammonium and the like.

R is also selected from alkoxycarbonyl ($-COOR^5$) wherein $R^5$ is alkyl having 1-10 carbon atoms, carbamoyl ($-CONH_2$); substituted carbamoyl ($-CONR^6R^7$) wherein $R^6$ and $R^7$ are selected from the group consisting of hydrogen, lower alkyl having 1-4 carbon atoms and diloweralkylaminoalkyl having 4-7 carbon atoms.

A is selected from the group consisting of ethylene ($-CH_2CH_2-$), trimethylene ($-CH_2CH_2CH_2-$), α-methylethylene ($-CH_2-CH(CH_3)-$), β-methylethylene ($-CH(CH_3)CH_2-$), α,α-dimethylethylene ($-CH_2-C(CH_3)_2-$), β,β-dimethylethylene ($-C(CH_3)_2CH_2-$) and oxymethylene ($-O-CH_2-$). (Note that when A consists of a two carbon bridge, the term α refers to the carbon adjacent to R, while β refers to the other carbon atom.)

R' is selected from the group consisting of formyl, acetyl, propionyl, acryloyl, hydroxyacetyl, or trifluoroacetyl.

Z is selected from the group consisting of ethylene ($-CH_2-CH_2-$), vinylene ($-CH=CH-$) and ethynylene ($-C \equiv C-$).

$R^2$ is selected from the group consisting of hydrogen and lower alkanoyl, e.g., formyl, acetyl, propionyl, butyryl, isobutyryl, valeryl, pivaloyl, and the like.

$R^3$ is the same or different and is selected from the group consisting of hydrogen and methyl.

$R^4$ is selected from the group consisting of hydrogen, lower alkyl of 1-4 carbon atoms either straight or branched chain (e.g., methyl, ethyl, propyl, isopropyl, butyl, tert-butyl), vinyl and 2,2,2-trifluoroethyl.

A preferred embodiment of this invention relates to the 8-aza-11,12-secoprostaglandins having the following general formula:

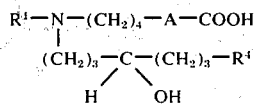

wherein $R^1$, A, and $R^4$ are as defined in formula I. An even more preferred embodiment encompasses compounds of formula II, wherein $R^1$ is acetyl or propionyl; A is ethylene or oxymethylene; and $R^4$ is ethyl, isopropyl, or butyl.

It is to be noted that the carbon atom bearing the $OR^2$ group in formula I and the one bearing the hydroxyl group in formula II is asymmetric. This invention also covers stereoisomers in which this asymmetric center is exclusively in either one or the other of the two possible configurations, R and S.

BACKGROUND OF THE INVENTION

The compounds of formula I are described as 8-aza-11,12-secoprostaglandins because of their structural relationship to the naturally occurring prostaglandins.

The prostaglandins constitute a biologically prominent class of naturally occurring, highly functionalized $C_{20}$ fatty acids which are anabolized readily in a diverse array of mammalian tissues from three essential fatty acids; namely, 8,11,14-eicosatrienoic acid, 5,8,11,14-eicosatetraenoic acid and 5,8,11,14,17-eicosapentaenoic acid. Each known prostaglandin is a formal derivative of the parent compound, termed "prostanoic acid"; the latter is a $C_{20}$ fatty acid covalently bridged between carbons 8 and 12 such as to form a trans, vicinally-substituted cyclopentane in which the carboxy-bearing side chain is "alpha" or below the plane of the ring and the other side chain is "beta" or above the plane of the ring as depicted in formula III:

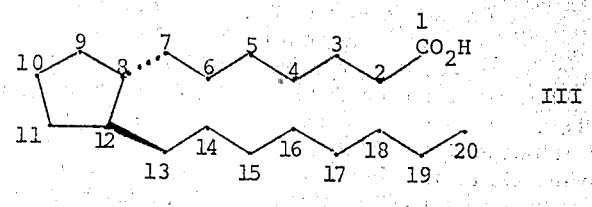

The six known primary prostaglandins, $PGE_1$, $PGE_2$, $PGE_3$, $PGF_{1\alpha}$, $PGF_{2\alpha}$, and $PGF_{3\alpha}$, resulting directly from anabolism of the above cited essential fatty acids via the action of prostaglandin synthetase, as well as the three prostaglandis resulting from in vivo dehydration of the PGE's, i.e., $PGA_1$, $PGA_2$, and $PGA_3$, are divided into three groups; namely, the PGE, PGF, and PGA series on the basis of three distinct cyclopentane nuclear sustitution patterns as illustrated as follows:

[E. W. Horton, Physiol. Rev., 49, 122 (1969)] and general clinical application [J. W. Hinman, Postgrad. Med. J., 46, 562 (1970)].

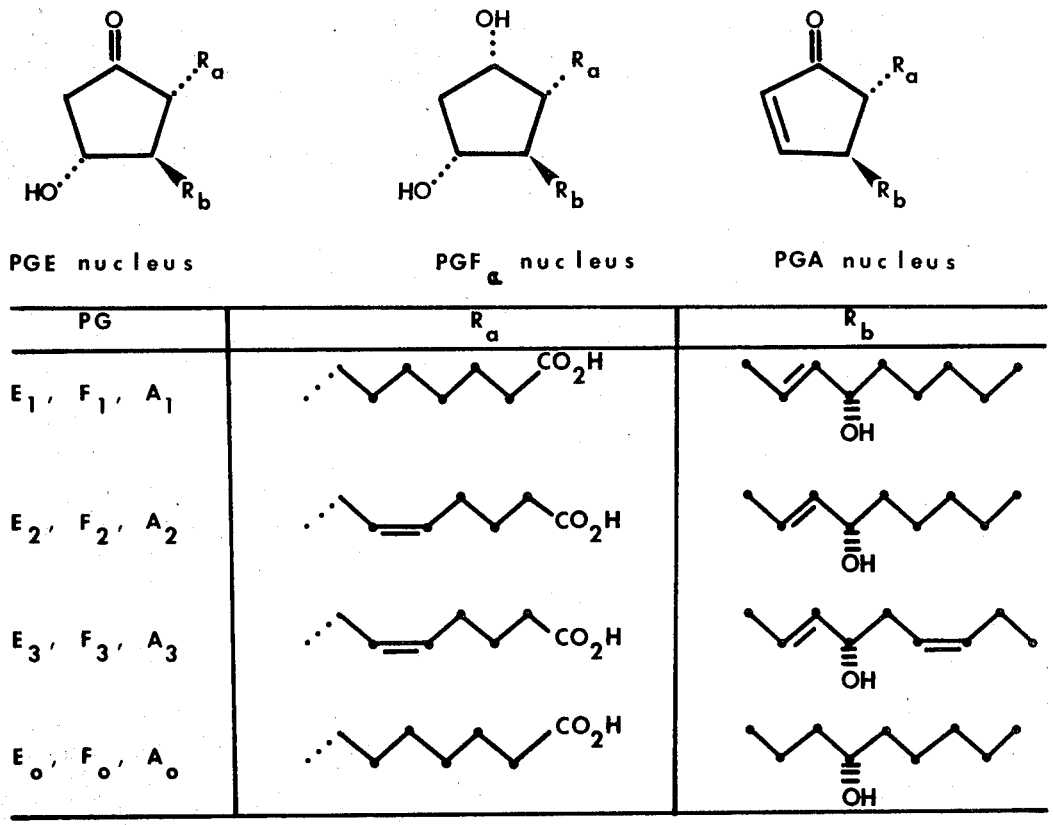

It should be noted that the Arabic subscripts designate the number of carbon-carbon double bonds in the designated compound and that the Greek subscript used in the PGF series designates the stereochemistry of the C-9 hydroxyl group.

Although the prostaglandins were discovered independently in the mid-1930's by Goldblatt [J. Chem. Soc. Chem. Ind. Lond., 52, 1056 (1933)] in England and Von Euler [Arch. Exp. Path. Pharmark., 175, 78 (1934)] in Sweden, these complex natural products received little attention from the scientific community until the early 1960's which coincides with the advent of modern instrumentation (e.g., mass spectrometry) which, in turn, was requisite for their successful isolation and structural elucidation by Bergström and colleagues [see Angew. Chem. Int. Ed., 4, 410 (1965) and references cited therein for an account of this work]. Within the last decade, a massive international scientific effort has been expended in developing both biosynthetic and chemical routes to the prostaglandins and, subsequently, in investigating of their biological activities. During this period, prostaglandins have been shown to occur extensively in low concentrations in a myriad of mammalian tissues where they are both rapidly anabolized and catabolized and to exhibit a vast spectrum of pharmacological activities including prominent roles in (a) functional hyperemia, (b) the inflammatory response, (c) the central nervous system, (d) transport of water and electrolytes, and (e) regulation of cyclic AMP. Further details concerning the prostaglandins can be found in recent reviews of their chemistry [J. E. Pike, Fortschr. Chem. Org. Naturst., 28, 313 (1970) and G. F. Bundy, A. Rep. in Med. Chem., 7, 157 (1972)], biochemistry [J. W. Hinman, A. Rev. Biochem., 41, 161 (1972)], physiological significance The potential application of natural prostaglandins as medicinally useful therapeutic agents in various mammalian disease states is obvious but suffers from three formidable major disadvantages, namely, (a) prostaglandins are known to be rapidly metabolized in vivo in various mammalian tissues to a variety of metabolites which are devoid of the desired original biological activities, (b) the natural prostaglandins are inherently devoid of biological specificity which is requisite for a successful drug, and (c) although limited quantities of prostaglandins are presently produced by both chemical and biochemical processes, their production cost is extremely high; and, consequently, their availability is quite restricted.

Our interest has, therefore, been to synthesize novel compounds structurally related to the natural prostaglandins but with the following unique advantages: (a) simplicity of synthesis leading to low cost of production; (b) specificity of biological activity which may be either of a prostaglandin-mimicking or prostaglandin-antagonizing type; (c) enhanced metabolic stability. The combination of these advantages serves to provide effective, orally and parenterally active therapeutic agents for the treatment of a variety of human and animal diseases. Included are applications in renal, cardiovascular, gastrointestinal, respiratory, and reproductive systems, and in the control of lipid metabolism, inflammation, blood clotting, skin diseases, and certain cancers.

More specifically, in the clinic, prostaglandin agonists can function as agents for improving renal function (e.g., renal vasodilation), antihypertensives, antiulcer agents, agents for fertility control, antithrombotics, antiasthmatics, antilipolytics, antineoplastic agents, and agents for the treatment of certain skin diseases.

Prostaglandin antagonists can function as anti-inflammatory agents, anti-diarrheal agents, antipyretics, agents for prevention of premature labor, and agents for the treatment of headache.

The compounds of the present invention are useful as pharmaceutically active compounds. Thus, these compounds are orally active in the treatment of conditions which are responsive to the actions of the natural prostaglandins. It is of course necessary to determine by routine laboratory testing which of the compounds of the present invention are most suitable for a specific end use. Some of the compounds of the invention have prostaglandin-like activity in that they mimic the effect of prostaglandin $E_1$ in stimulating the formation of cyclic AMP in the mouse ovary in vitro.

The compounds of this invention are particularly useful for improving renal function in that they are renal vasodilators and effect increased renal blood flow in laboratory animals. Certain of the compounds of this invention, e.g., 7-[N-(4-hydroxynonyl)acetamido]heptanoic acid, mimic the effects of prostaglandin $E_1$ and are useful on oral administration in producing increased renal blood flow (renal vasodilation) in laboratory animals and are useful in improving renal function in animals, e.g., dogs, with poorly-functioning kidneys.

Because of their biological activity and ready accessibility, the compounds of the invention are also useful in that they permit large scale animal testing useful and necessary to understanding of these various disease conditions such as kidney impairment, ulcers, dwarfism caused by poorly-functioning pituitary glands, stroke (thrombus formation) and the like. It will be appreciated that not all of the compounds of this invention have these biological activities to the same degree but the choice of any particular ones for any given purpose will depend upon several factors including the disease state to be treated.

The compounds of this invention can be administered either topically or systemically (i.e., intravenously, subcutaneously, intramuscularly, orally, rectally, or by aerosolization in the form of sterile implants for long action.

Whatever the mode of administration, doses in the range of about 0.10 to 20 milligrams per kilogram of body weight per day are used. The exact dose depends upon the age, weight, and condition of the patient, and the frequency and route of administration.

The low cost and ready accessibility of the compounds of this invention make them particularly promising for applications in veterinary medicine in which field their utilities are comparable to those in human medicine.

PROCESSES TO PREPARE THE COMPOUNDS OF THIS INVENTION

The new chemical compounds with which this invention is concerned are prepared by the following two processes. The first process involves the reaction of a compound such as III with a compound such as IV, wherein A, $R^1$, Z, $R^3$, and $R^4$ are as defined:

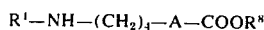

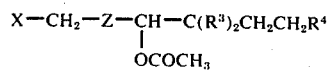

as in formula I above and $R^8$ is loweralkyl having 1–5 carbon atoms, preferably ethyl; and X is halogen, e.g., chloro, bromo, or iodo. The reaction is carried out by preparing the alkali metal salt of III by reaction of III with sodium hydride in a solvent such as a 1:1 mixture of benzene and dimethylformamide, adding compound IV at ambient temperature, then heating the reaction mixture at 50°–100° C. for from one to twenty hours. This reaction scheme affords intermediates represented by formula V:

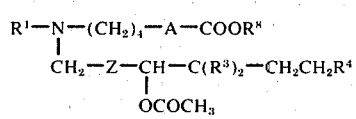

Mild basic hydrolysis (NaOH in aqueous methanol or ethanol) of the ester functions of compound V affords compounds of formula I, e.g., VI:

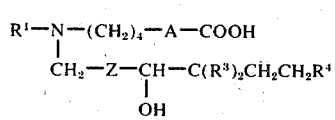

In the second process a compound such as VII is caused to react with a compound of formula VIII, wherein A, R, and $R^1$ are defined as in formula I above, X is halogen, e.g., chloro, bromo, or iodo, $R^5$ is loweralkyl having 1–5 carbon atoms, preferably ethyl, and THP is the 2-tetrahydropyranyl group. The reaction is carried

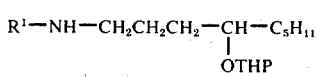

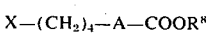

out by preparing the alkali metal salt of VII by reaction of VII with sodium hydride in a solvent such as a 1:1 mixture of benzene and dimethylformamide, adding compound VIII at ambient temperature then heating the reaction at 50°–100° C. for from 1–20 hours. This reaction scheme affords intermediates represented by formula IX:

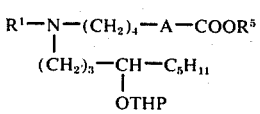

Mild acid hydrolysis (aqueous HCl in methanol or ethanol) removes the tetrahydropyranyl protecting group, then mild basic hydrolysis (NaOH in aqueous methanol or ethanol) of the ester function affords compounds of formula I, e.g., X:

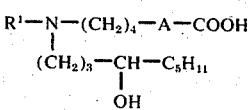

It is frequently advantageous from a therapeutic standpoint to prepare compounds of this invention (formula I) in which the asymmetric carbon atom which bears $OR^2$ is exclusively in the R or S configuration. It will be recalled that the corresponding center in the natural prostaglandins is in the S configuration; inversion of this center may or may not produce a reduction in biological activity, although a marked increase in biological specificity is often realized.

In our series of 8-aza-11,12-secoprostaglandins, compounds which are exclusively R or S at this center can be produced by employing pre-resolved compounds IV or VII and carrying out the steps of process 1 or 2. An example of the use of such a pre-resolved compound IV is given under the section "Preparation of Intermediates (Example J)".

DERIVATIZATION OF PRODUCTS

The directly obtained products of the processes described supra can be derivatized to yield the other products of formula I.

1. The fundamental processes yield compounds where R is carboxy. To obtain carboxy salts the acid products are dissolved in a solvent such as ethanol, methanol, glyme and the like and the solution treated with an appropriate alkali or alkaline earth hydroxide or alkoxide to yield the metal salt, or with an equivalent quantity of ammonia, amine or quaternary ammonium hydroxide to yield the amine salt. In each instance, the salt either separates from the solution and may be separated by filtration or, when the salt is soluble it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine or a quaternary ammonium hydroxide.

To obtain carboxy esters (i.e., compounds where R is alkoxycarbonyl) the acid products are treated in ether with an ethereal solution of the appropriate diazoalkane. For example, methyl esters are produced by reaction of the acid products with diazomethane. To obtain products where R is carbamoyl or substituted carbamoyl, the acid product is first converted to an active Woodward ester. For example, the acid product can be made to react with N-tert-butyl-5-methylisoxazolium perchlorate in acetonitrile in the presence of a base such as triethylamine to yield an active ester in which R is

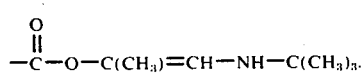

Active esters of this type can be reacted with ammonia to yield products of formula I where R is carbamoyl, with primary or secondary amines or di-lower-alkylaminoalkylamines to yield products where R is substituted carbamoyl, i.e., $-CONR^6R^7$.

2. The fundamental process yields products where $R^2$ is hydrogen. In compounds of formula X, reaction with formic acid, acetic anhydride, propionic anhydride, butyric anhydride, isobutyric anhydride, valeric anhydride, pivalic anhydride and the like, without solvent and at temperatures from 25° to 60° C., gives compounds wherein $R^2$ is formyl, acetyl, propionyl, butyryl, isobutyryl, valeryl, and pivaloyl, respectively.

PREPARATION OF STARTING MATERIALS

1. The reagent III which has the general formula shown, wherein $R^1$ and $R^8$ are as defined previously, is prepared in the following manner. The corresponding amino-

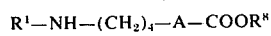

acid is treated with the appropriate anhydride, $R^1COOCOR^1$, and the resulting acylated compound is esterified in the appropriate alcohol, $R^8OH$.

2. The reagent IV A which has the following general formula wherein X is halogen and $R^3$ and $R^4$ are as

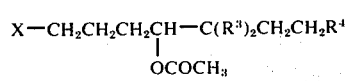

previously defined is prepared in the following manner. A Grignard reagent $R^4CH_2CH_2(R^3)_2C-MgI$ or $R^4CH_2CH_2(R^3)_2C-MgBr$ is allowed to react, in ether, with a nitrile $X(CH_2)_3CN$. The resulting imine is hydrolyzed in aqueous acidic solution to give ketone of the formula $X(CH_2)_3C(=O)C(R^3)_2CH_2CH_2R^4$. The ketones are reduced to the corresponding alcohols $X(CH_2)_3CH(OH)-C(R^3)_2CH_2CH_2R^4$ with sodium or potassium borohydride in a suitable solvent such as methanol, ethanol or diglyme. Acetylation of these alcohols, preferably with acetic anhydride, yields the reagent IV A.

The reagent IV B which has the following general formula $$X-CH_2-Z''-CH-C_5H_{11} \quad \text{IV B}$$
$$\qquad\qquad\qquad |$$
$$\qquad\qquad\quad OCOCH_3$$

wherein X is halogen and $Z''$ is $-C\equiv C-$ is prepared in the following manner. 1-Octyn-3-ol is treated with acetic anhydride to give the acetylated alcohol

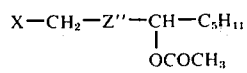

This compound is treated with paraformaldehyde and diethylamine to afford the tertiary amine

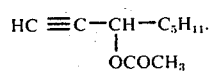

which when treated with cyanogen bromide yields the reagent IV B. The analogues having longer or shorter chains are prepared in the same manner.

By using the resolved R and S forms of the 1-octyn-3-ol in the above scheme, the corresponding R and S forms of the reagent IV B can be obtained.

It should be noted here that the use of the R or S enantiomers of reagent IV B produce the R and S enantiomers, respectively, of compounds of formula VI A wherein $R^1$ is as defined as in formula I above and $Z''$ is $-C\equiv C-$.

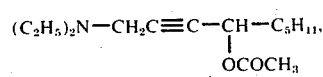

These optically active products VI A can be hydrogenated over a platinum catalyst to give the R and S enantiomers of compounds of formula VI A where Z is ethylene, $-CH_2-CH_2-$.

The reagent IV C which has the following general formula

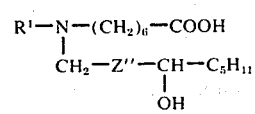

wherein X is halogen is prepared in the following manner. A Grignard reagent $C_5H_{11}MgBr$ or $C_5H_{11}MgI$ is allowed to react with crotonaldehyde to give, after hydrolysis, the alcohol $CH_3CH=CH-CH(OH)C_5H_{11}$. This alcohol is acetylated, preferably with acetic anhydride without solvent at 30°-100° C. for 2-12 hours, to give the intermediate $CH_3CH=CH-CH(OCOCH_3)C_5H_{11}$. This intermediate is allowed to react with N-bromosuccinimide in chloroform at 50°-70° C. for 2.5 to 5 hours to effect allylic bromination and give the reagent of formula IV C. As before, longer or shorter chain analogues are prepared using the corresponding Grignard reagent.

3. The reagent VII which has the formula shown is prepared by the following reactions. The alcohol prepared

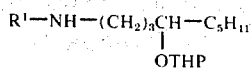  VII in Section 2 above with the formula

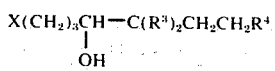

(with $R^3$=H and $R^4$=$CH_2CH_3$) is treated with dihydropyran and a catalytic amount of acid to give

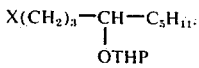

Treatment of this halo compound with the sodium salt of phthalimide in dimethylformamide affords the corresponding phthalimido compound. Cleavage of this compound with hydrazine in ethanol yields the amine

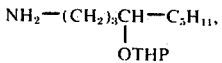

which upon acetylation with acetic anhydride in pyridine affords the reagent VII. As before, the chain length can be varied by choice of suitable starting materials.

4. The preparation of reagents of formula VIII has been described in the scientific and patent literature in instances

  VIII where A is ethylene, trimethylene, α-methylethylene, β-methylethylene, α,α-dimethylethylene, β,β-dimethylethylene. To prepare reagents where A is oxymethylene, an ester of glycolic acid, $HOCH_2COOR^5$ is treated with a strong base, preferably sodium hydride, in a non-protic solvent (dimethylformamide, glyme, and the like) and the resulting anion caused to react with a 1,4-dihalobutane, preferably 1,4-dibromobutane. The glycolic ester and base are employed in approximately equimolar quantities; a 1.5 to 2 molar excess of the dihalobutane is advantageously used.

5. Method for obtaining optical antipodes of some compounds of this invention have been described supra whereby one of the components of the molecule is preresolved prior to its assembly into the whole molecule. Other methods also can be employed; for example, mixtures of racemates may be separated by taking advantage of the physiochemical differences between the components using chromatography and/or fractional crystallization. The racemic products and intermediates of this invention can be resolved into their optically active components by any one of a number of methods of resolution which are well described in the chemical literature.

Those compounds which are carboxylic acids can be converted to the diastereoisomeric salts by treatment with an optically active base as + or -α-methylbenzylamine, + or - α-(1-naphthyl)-ethylamine, brucine, cinchonine, cinchonidine, or quinine. These diastereoisomeric salts can be separated by fractional crystallization.

The carboxylic acids of this invention also can be converted to esters using an optically active alcohol, such as, estradiol-3-acetate, or d- or l-menthol and the diastereoisomeric esters resolved by crystallization or by chromatographic separation.

Racemic carboxylic acids also may be resolved by reverse phase and absorption chromatography using an optically active support and absorbent.

Compounds of this invention which contain free hydroxyl groups can be esterified with acid chlorides or anhydrides derived from optically active acids, such as, (+)-10-camphorsulfonic acid, (+)-α-bromocamphor-π-sulfonic acid, or d- or l-6,6'-dinitrodiphenic acid to form esters which can be resolved by crystallization.

Another method of obtaining pure optical isomers involves incubation of the racemic mixture with certain microorganisms such as fungi, by processes well established in the art, and recovering the product formed by the enzymatic transformation.

The methods described supra are especially effective if one applies the process to a compound where one asymmetric center has been preresolved by the techniques already described.

This invention is further described in the following examples.

PREPARATION OF INTERMEDIATES

A. Preparation of 1-Chloro-4-acetoxynonane

Step 1. Preparation of 1-Chloro-4-nonanone

To the Grignard reagent prepared from a mixture of amyl bromide (226.59 g.; 1.5 moles) and magnesium (36.48 g.; 1.5 moles) in ether (1000 ml.) is added, dropwise, during one hour, 4-chlorobutyronitrile (155.34 g.; 1.5 moles). Stirring is continued for an additional one hour. The reaction mixture is poured into a mixture of finely crushed ice (1000 g.) and concentrated hydrochloric acid (750 ml.). The ether layer is separated quickly and discarded. The aqueous layer is heated on a steam bath for one hour to hydrolyze the intermediate imine and cause the separation of the ketone as an oil. After cooling, the oil is extracted with ether and the combined extracts are washed with saturated sodium chloride solution and dried over anhydrous sodium sulfate. The solvent is removed under vacuum and the residual oil is distilled to give 69.0 g. (26%) of colorless oil, b.p. 115°–117°/14 mm.; pmr ($CDCl_3$) δ 0.90 (3H,t), 3.56 (2H,t,$CH_2Cl$).

Step 2. Preparation of 1-Chloro-4-nonanol

A suspension of sodium borohydride (6.62 g.; 0.175 mole) and sodium hydroxide (1.3 g.) in ethanol (310 ml.) is treated, dropwise, over 1 hour with 1-chloro-4-nonanone (61.40 g.; 0.349 mole) while the temperature is maintained at 45°–50°. Stirring is continued for one hour, without external cooling.

The reaction mixture is acidified with concentrated hydrochloric acid to the Congo red endpoint and then the ethanol is removed under reduced pressure. The residue is treated with water (200 ml.) and the resulting oil is extracted with ether. The combined extracts are washed with saturated sodium chloride solution and dried over anhydrous sodium sulfate. The solvent is removed under vacuum to give the title compound as a light-yellow residual oil, yield 58.85 g.; ir (neat) 3400 $cm^{-1}$.

Step 3. Preparation of 1-Chloro-4-acetoxynonane

A mixture of 1-chloro-4-nonanol (111.99 g.; 0.627 mole) and acetic anhydride (128.0 g.; 1.254 moles) is heated on a steam bath for 1½ hours.

The volatile materials are removed under reduced pressure and the residual oil is distilled to give 88.6 g. (64%) of colorless oil, b.p. 130°–133°/14 mm.; pmr (CDCL$_3$) δ 0.89 (3H,t), 2.02 (3H,s CH$_3$COO), 3.53 (2H,t CH$_2$Cl), 4.89 (1H,m). Anal. Calcd. for C$_{11}$H$_{21}$ClO$_2$: c, 59.85; H,9.59. Found: C, 59.87; H, 9.67.

B. Preparation of 1-Chloro-4-acetoxy-8-methylnonane

Step 1. Preparation of 1-Chloro-8-methyl-4-nonanone

To the Grignard reagent prepared from a mixture of 1-bromo-4-methylpentane (200.00 g; 1.21 mole) and magnesium (29.43 g.; 1.21 mole) in ether (800 ml.) is added, dropwise during one hour, 4-chlorobutyronitrile (125.30 g.; 1.21 mole). Stirring is continued for an additional one hour.

The reaction mixture is poured into a mixture of finely crushed ice (800 g.) and concentrated hydrochloric acid (600 ml.). The ether layer is separated quickly and discarded. The aqueous layer is heated on a steam bath for one hour to hydrolyze the intermediate imine and cause the separation of the ketone as an oil. After cooling, the oil is extracted with ether and the combined extracts are washed with saturated sodium chloride solution and dried over anhydrous sodium sulfate. The solvent is removed under vacuum and the residual oil is distilled to give 23.3 g. (10%) of colorless oil, b.p. 121–122°/15 mm; pmr (CDCl$_3$)δ 0.89 (6H,d), 3.57 (2H,t CH$_2$Cl).

Anal. Calcd. for C$_{10}$H$_{19}$ClO: C, 62,98; H, 10.04. Found: C, 62.86; H, 10.20.

Step 2. Preparation of 1-Chloro-8-methyl-4-nonanol

A suspension of sodium borohydride (2.3 g., 0.061 mole) and sodium hydroxide (0.5 g.) in ethanol (110 ml.) is treated dropwise during one hour with 1-chloro-8-methyl-4-nonanone (23.0 g., 0.121 mole) while the temperature is maintained at 45°–50°C. Stirring is continued for one hour without external cooling.

The reaction mixture is acidified with concentrated hydrochloric acid to the Congo Red endpoint and then the ethanol is removed under reduced pressure. The residue is treated with water (70 ml.) and the resulting oil is extracted with ether. The combined extracts are washed with saturated sodium chloride solution and dried over anhydrous sodium sulfate. The solvent is removed under vacuum to give the title compound as a light yellow residual oil, yield 22.73 g.; ir (neat) 3400 cm$^{-1}$.

Step 3. Preparation of 1-Chloro-4-acetoxy-8-methylnonane

A mixture of 1-chloro-8-methyl-4-nonanol (22.73 g; 0.118 mole) and acetic anhydride (24.07 g.; 0.236 mole) is heated on a steam bath for 1½ hours.

The volatile materials are removed under reduced pressure and the residual oil is distilled to give 14.58 g. (58%) of colorless oil, b.p. 138°–139°/15 mm.; pmr (CDCl$_3$)δ 0.85 (6H,d), 2.02 (3H,s CH$_3$COO), 3.53 (2H,t CH$_2$Cl), 4.92 (1H,m).

C. Preparation of 1-Chloro-4-acetoxyundecane

Step 1. Preparation of 1-Chloro-4-undecanone

This compound is prepared essentially by the same procedure as described for 1-chloro-4-nonaone (Example A, Step 1) using the following reagents:

| | |
|---|---|
| 1-Bromoheptane | 214.94 g. (1.2 mole) |
| Magnesium | 29.18 g (1.2 mole) |
| Ether | 800 ml. |
| 4-Chlorobutyronitrile | 124.27 g (1.2 mole) |

The title compound is obtained as a colorless oil, yield 60.4 g. (15%), b.p. 135°–140°/15 mm.; pmr (CDCl$_3$)δ 0.93, (3H,t), 3.57 (2H,t CH$_2$Cl).

Step 2. Preparation of 1-Chloro-4-undecanol

This compound is prepared essentially by the same procedure as described for 1-chloro-4-nonanol (Example A, Step 2) using the following reagents:

| | |
|---|---|
| Sodium borohydride | 5.56 g. (0.147 mole) |
| Sodium hydroxide | 1.12 g. |
| Ethanol | 265 ml. |
| 1-Chloro-4-undecanone | 60.00 g. (0.294 mole) |

The title compound is obtained as a yellow residual oil, yield 60.02 g.

Step 3. Preparation of 1-Chloro-4-acetoxyundecane

This compound is prepared essentially by the same procedure as described for 1-chloro-4-acetoxy-nonane (Example A, Step 3), using the following reagents:

| | |
|---|---|
| 1-Chloro-4-undecanol | 60.02 g. (0.29 mole) |
| Acetic anhydride | 59.16 g. (0.58 mole) |

The title compound is obtained as a colorless oil, yield 44.6 g. (62%), b.p. 155°–158°/15 mm.; pmr (CDCl$_3$)δ 0.88 (3H,t), 2.02 (3H,s CH$_3$COO), 3.53 (2H,t CH$_2$Cl), 4.92 (1H,m).

Anal. Calcd. for C$_{13}$H$_{25}$ClO$_2$: C, 62.76; H, 10.13. Found: C, 63.03; H, 10.40.

D. Preparation of 1-Chloro-4-acetoxy-8,8-dimethyl-nonane

By following the procedure described for 1-chloro-4-acetoxynonane (Example A) but substituting 1-bromo-4,4-dimethylpentane for amyl bromide, there is obtained in succession: 1-chloro-8,8-dimethyl-4-nonanone, 1-chloro-8,8-dimethyl-4-nonanol, and 1-chloro-4-acetoxy-8,8-dimethylnonane.

E. Preparation of 1-Chloro-4-acetoxy-9,9,9-trifluorononane

By following the procedure described for 1-chloro-4-acetoxynonane (Example A) but substituting 1-bromo-5,5,5-trifluoropentane for amyl bromide, there is obtained in succession: 1-chloro-9,9,9-trifluoro-4-nonanone, 1-chloro-9,9,9-trifluoro-4-nonanol, and 1-chloro-4-acetoxy-9,9,9-trifluoronane.

F. Preparation of 1-Chloro-4-acetoxy-8-nonene

By the following the procedure described for 1-chloro-4-acetoxynonane (Example A) but substituting 1-bromo-4-pentane for amyl bromide, there is obtained in succession: 1-chloro-8-nonen-4-one, 1-chloro-8-nonen-4-ol, and 1-chloro-4-acetoxy-8-nonene.

G. Preparation of 1-Chloro-4-acetoxy-5,5-dimethylnonane

Step 1. Preparation of 1-Chloro-5,5-dimethyl-4-nonanone

Four hundred ml. of a solution in ether of 1,1-dimethylpentylmagnesium chloride prepared from magnesium (24.3 g, 1.0 mole) and 1-chloro-1,1-dimethylpentane (134.5 g., 1.0 mole) according to the procedure of Whitmore and Badertscher [J. Am. Chem. Soc., 55, 1559 (1933)] is added dropwise with stirring to 4-chlorobutyryl chloride (197 g., 1.4 moles) in ether (400 ml.) during 6 hours. The reaction mixture is stirred for an additional 12 hours. It is then poured into a mixture of ice and dilute hydrochloric acid. The ether layer is separated, washed with water and brine and dried over sodium sulfate. The ether is evaporated and the residue distilled at aspirator vacuum through a Vigreaux column to yield the product as a colorless oil.

Step 2. Preparation of 1-Chloro-5,5-dimethyl-4-nonanol

By following the procedure described for 1-chloro-4-nonanol (Example A, Step B) but substituting 1-chloro-5,5-dimethyl-4-nonanone for 1-chloro-4-nonanone and continuing stirring and heating at 50° for 6 hours, there is obtained 1-chloro-5,5-dimethyl-4-nonanol.

Step 3. Preparation of 1-Chloro-4-acetoxy-5,5-dimethylnonane

By following the procedure described for 1-chloro-4-acetoxynonane (Example A, Step 3) but substituting 1-chloro-5,5-dimethyl-4-nonanol for 1-chloro-4-nonanol and continuing the steam bath heating for 4 hours, there is obtained 1-chloro-4-acetoxy-5,5-dimethylnonane.

H. Preparation of 1-Bromo-4-acetoxy-2-nonene

A mixture of 4-acetoxy-2-nonene (73.5 g., 0.4 mole), N-bromosuccinimide (80.0 g., 0.45 mole), and carbon tetrachloride (500 ml.) is boiled under reflux for 3 hours. The mixture is then cooled and the suspended succinimide, removed by filtration. The carbon tetrachloride solution is washed with dilute sodium bicarbonate solution and water, and is dried over sodium sulfate. The carbon tetrachloride is evaporated in vacuo and the residual oil is distilled to yield 62 g. (59%) of 1-bromo-4-acetoxy-2-nonene as a light yellow oil, b.p. 110°–12°/0.1 mm.

I. Preparation of 1-Bromo-4-acetoxy-2-nonyne

Step 1. Preparation of 3-Acetoxy-1-octyne

1-Octyn-3-ol (100 g., 0.794 mole) is dissolved in pyridine (79 g., 1.0 mole) and acetic anhydride (81.6 g., 0.80 mole) is added dropwise with stirring during one hour. The temperature rises to 45°. The solution is heated at 55° for one hour and is then cooled and poured into 200 ml., ice-cold 5% hydrochloric acid. The oily product is taken up in ether, washed with water and brine and dried over sodium sulfate. The ether is evaporated and the residual oil distilled to yield 106.4 g. (80%) of 3-acetoxy-1-octyne, b.p. 91°–92°/15 mm.

Step 2. Preparation of 1-Diethylamino-4-acetoxy-2-nonyne

A mixture of 3-acetoxy-1-octyne (58.8 g., 0.35 mole), diethylamine (28.5 g., 0.39 mole), paraformaldehyde (13.8 g., 0.46 mole) and p-dioxane (60 ml.) is heated on the steam bath under a reflux condenser for 17 hours. The resulting solution is cooled and diluted with 250 ml. of ether. The solution is extracted with 300 ml. of 5% hydrochloric acid. The acidic aqueous extract is made basic with 10% sodium hydroxide solution. The liberated amine is taken up in ether, washed with water and brine and dried over sodium sulfate. The ether is evaporated and the residual oil distilled to yield 73.1 g. (89%) of 1-diethylamino-4-acetoxy-2-nonyne, b.p. 103°–109°/0.3 mm.

Anal. cald. for $C_{15}H_{27}NO_2$: C, 71.10; H, 10.74; N, 5.33. Found: C, 70.73; H, 11.03; N, 5.55.

Step 3. Preparation of 1-Bromo-4-acetoxy-2-nonyne

A solution of 1-diethylamino-4-acetoxy-2-nonyne (50.6 g., 0.20 mole) and cyanogen bromide (21.2 g., 0.20 mole) in ether (250 ml.) is allowed to stand at 25°–27° for 18 hours. The ether solution is washed with 5% hydrochloric acid solution, water, and brine and dried over sodium sulfate. The ether is evaporated and the residual oil distilled. After a forerun of diethylcyanamide, there is collected 34.1 g. (65%) of 1-bromo-4-acetoxy-2-nonyne, b.p. 97°–105°/0.2 mm.

Anal. calcd. for $C_{11}H_{17}BrO_2$: C, 50.59; H, 6.56. Found: C, 50.54; H, 6.49.

J. Preparation of 1-Bromo-4(R)-acetoxy-2-nonyne

By the following the procedure described in Example H but substituting (R)-1-octyn-3-ol $[\alpha]_D^{26}$ + 6.1° [C 3.1, CHCl$_3$] for the racemic 1-octyn-3-ol, there is obtained successively: 3(R)-acetoxy-1-octyne, $[\alpha]_D^{26}$ + 70° [C 3.1, CHCl$_3$], 1-diethylamino-4(R)-acetoxy-2-nonyne, $[\alpha]_D^{26}$ + 74° [C 3.2, CHCl$_3$], and 1-bromo-4(R)-acetoxy-2-nonyne, $[\alpha]_D^{26}$ + 75° [C, 3.2, CHCl$_3$].

K. Preparation of 1-Bromo-4(S)-acetoxy-2-nonyne

By following the procedure described in Example H but substituting (S)-1-octyn-3-ol, $[\alpha]_D^{26}$ − 6.4° [C 3.3, CHCl$_3$], for the racemic 1-octyn-3-ol, there are obtained successively: 3(S)-acetoxy-1-octyne, $[\alpha]_D^{26}$ − 79° [C 3.0, CHCl$_3$], 1-diethylamino-4(S)-acetoxy-2-nonyne, $[\alpha]_D^{26}$ − 80° (C 3.3, CHCl$_3$], and 1-bromo-4(S)-acetoxy-2-nonyne, $[\alpha]_D^{26}$ − 83° [3.7, CHCl$_3$].

L. Preparation of Methyl 7-bromo-2-methylheptanoate

Step 1. Preparation of 5-Acetoxypentyl chloride

Acetic anhydride (102 g., 1 mole) is added dropwise with stirring to pentamethylene chlorohydrin (90 g., 0.74 mole). The resulting solution is heated on the steam bath for one hour and allowed to stand overnight at room temperature. The reaction mixture is distilled to yield 83.6 g. (69%) of 5-acetoxypentyl chloride, b.p. 101°–104°/20 mm.

Step 2. Preparation of Diethyl (5-Acetoxypentyl)methylmalonate

Sodium hydride (4.8 g., 0.2 mole) as a 50% suspension in mineral oil is washed with petroleum ether under nitrogen to remove the mineral oil, suspended in dry benzene (150 ml.), and the suspension cooled in an ice bath. Diethyl methylmalonate (34.8 g., 0.2 mole) dissolved in sieve dried DMF (150 ml.) is added to the suspension of sodium hydride dropwise. The mixture is allowed to stand overnight at room temperature. Potassium iodide (0.4 g.) and 5-acetoxypentyl chloride (32.9 g., 0.2 mole) are then added, and the mixture is heated for 24 hours at 125° in an oil bath. The reaction mixture is concentrated in vacuo, diluted with ether (200 ml.), and filtered to remove sodium chloride. The filtrate is washed with brine, dried over anhydrous magnesium sulfate and concentrated to yield 39.6 g. (66%) of oily diethyl (5-acetoxypentyl)methylmalonate.

Step 3. Preparation of 7-Bromo-2-methylheptanoic acid

A mixture of the crude diethyl (5-acetoxypentyl)methylmalonate (68 g., 0.23 mole) and 48% aqueous hydrobromic acid (100 ml.) is refluxed for 20 hours. The mixture is then concentrated by distillation until the internal temperature rises to 120°; 96 ml. of distillate (2 layers) is collected. The residual liquid is cooled, dissolved in ether, washed with brine, dried over magnesium sulfate, and the solution concentrated in vacuo to yield 54 g. of crude 7-bromo-2-methylheptanoic acid as a dark viscous liquid.

Step 4. Preparation of Methyl 7-Bromo-2-methylheptanoate

A solution of crude 7-bromo-2-methylheptanoic acid (54 g., 0.24 mole) and concentrated sulfuric acid (2 drops) in absolute methanol (300 ml.) is refluxed for 5 hours. After standing overnight at room temperature, the solution is concentrated in vacuo and diluted with water. The mixture is made basic by the addition of saturated sodium carbonate solution and the product taken up in ether. The ether extract is washed with water, dried over anhydrous magnesium sulfate and distilled to yield 11.8 g. (16%) of methyl 7-bromo-2-methylheptanoate, b.p. 67–70°/0.05 mm.; pmr (CDCl$_3$)δ 1.13 (3H,d 2-CH$_3$), 2.42 (1H,m C$\underline{H}$COOCH$_3$), 3.38 (2H,t CH$_2$Br), 3.65 (3H,s CH$_3$O).

M. Preparation of Ethyl 4-Bromobutoxyacetate

Sodium hydride (9.0 g., 0.375 mole) is suspended in 1,2-dimethoxyethane. The mixture is stirred and cooled in an ice bath while ethyl glycollate (39.0 g., 0.375 mole) is added dropwise during one hour. 1,4-Dibromobutane (108 g., 0.5 mole) is added all at once to the resulting thick suspension. The mixture is warmed gently to initiate a strongly exothermic reaction; then the mixture is heated 3 hours on the steam bath. The mixture is poured into cold water. The heavy oil layer is taken up in ether, washed with three portions of water, and dried over sodium sulfate.

Evaporation of the ether and distillation of the residual oil yields 21.3 g. (24%) of ethyl 4-bromobutoxyacetae, a colorless oil, b.p. 99°–103°/0.2 mm.

N. Preparation of N-[4-(2-Tetrahydropyranyloxy)nonyl]-acetamide

Step 1. Preparation of 1-Chloro-4-(2-tetrahydropyranyloxy)nonane

To a stirred solution of 1-chloro-4-hydroxynonane (Example A, Step 2) (11.0 g., 0.062 mole) and dihydropyrane (5.2 g., 0.062 mole), cooled in an ice bath is added 5 drops of hydrochloric acid (conc.). A slight exothermic reaction is noted and when this is complete the reaction is allowed to come to room temperature then stand at this temperature for 2 hours. At the end of this period, several pellets of sodium hydroxide are added and the reaction is distilled in vacuo. The yield of 1-chloro-4-(2-tetrahydropyranyloxy)nonane is 12.5 g. (77%), boiling 96°–102°C./0.1 mm. Upon redistillation, a boiling point of 90°–92°C./0.1 mm. is obtained.

Step 2. Preparation of N-[4-(2-Tetrahydropyranyloxy)nonyl]phthalimide

Sodium hydride (53%) (1.5 g. excess) is washed with benzene three times by decantation, then dimethyl formamide (100 ml.) is added. To this stirred suspension is added a solution of phthalimide (4.3 g., 0.03 mole) in dimethyl formamide (50 ml.) at such a rate as to keep the temperature below 35°C. A clear solution is obtained and to it is added 1-chloro-4-(2-tetrahydropyranyloxy)-nonane (7.8 g., 0.03 mole) and the resulting clear solution is stirred and heated at 95°C. for 20 hours. The reaction is then concentrated to one half its volume in vacuo, poured into ice water (200 ml.) and extracted with ether (2 × 150 ml.). The ether is washed with 5% sodium hydroxide (2 × 50 ml.), saturated sodium chloride solution (2 × 50 ml.) then dried over sodium sulfate. Evaporation of the ether affords 4.5 g. (45% yield) of N-[4-(2-tetrahydropyranyloxy)nonyl]phthalimide melting 59°–61°C. After recrystallization from cyclohexane, the product melts at 62°–63°C.

Anal. calcd. for C$_{22}$H$_{31}$NO$_4$: C, 70.75; H, 8.36; N, 3.75. Found: C, 71.03; H, 8.28; N, 3.81.

Step 3. Preparation of 4-(2-Tetrahydropyranyloxy)nonylamine

To a solution of N-[4-(2-tetrahydropyranyloxy)-nonyl]phthalimide (33.0 g., 0.88 mole) in absolute ethanol (300 ml.) is added hydrazine (64%) (10 ml. excess) and the reaction is heated at reflux for 1.5 hours. An additional 5 ml. of hydrazine (64%) is added and reflux continued for 1.5 hours. The reaction is cooled to room temperature and the white solid that is present is removed by filtration. The filtrate is concentrated in vacuo to 75 ml. then poured into water (200 ml.). The solution is made basic with 5% sodium hydroxide and then extracted with ether (3 × 100 ml.). The ether layer is washed with saturated sodium chloride solution then dried over sodium sulfate. The ether is removed in vacuo and the resulting oil is distilled. The yield of 4-(2-tetrahydropyranyloxy)nonylamine is 16.0 g. (75%), boiling 102°–104°/0.01 mm.

Analysis calcd. for C$_{14}$H$_{29}$NO$_2$: C, 69.08; H, 12.01; N, 5.75. Found: C, 68.58; H, 12.42; N, 5.66

Step 4. Preparation of N-[4-(2-Tetrahydropyranyloxy)nonyl]acetamide

To a stirred, ice cold solution of 4-(2-tetrahydropyranyloxy)nonylamine (7.29 g., 0.03 mole) in pyridine (40 ml.) is added acetic anhydride (3.06 g., 0.03 mole) at such a rate as to maintain the reaction temperature at 5°–10°C. The reaction is then allowed to stand at room temperature for 6 hours, poured into ice water (200 ml.) and extracted with ether (2 × 100 ml.). The ether is extracted with ice cold 5% hydrochloric acid (2 × 20 ml.), washed with brine (2 × 25 ml.), then dried over sodium sulfate. Evaporation in vacuo affords the subject compound as a pale yellow oil.

EXAMPLE 1

Preparation of 7-[N-(4-Hydroxynonyl)acetamido]heptanoic acid

Step A. Preparation of Ethyl 7-{N-[4-(2-tetrahydroxypyranyloxy)nonyl-]acetamido}heptanoate A stirred suspension of sodium hydride (57%) in mineral oil (8.84 g., 0.21 mole) in a solvent mixture of benzene (75 ml.) and dimethylformamide (75 ml.) is treated, over 30 minutes with N-[4-(2-tetrahydropyranyloxy)nonyl]-acetamide (Example N, Step 4) (57.2 g., 0.20 mole). Stirring is continued for 30 minutes. Then ethyl 7-bromoheptanoate (49.8 g., 0.21 mole) is added dropwise, and the reaction is heated at 100° C. for 4.5 hours.

The cooled reaction is poured into water (350 ml.) and the organic layer is separated. The aqueous layer is extracted with ether (200 ml.). The combined organic solutions are washed with saturated sodium chloride solution and then dried over sodium sulfate. The solvent are removed under vacuum to give ethyl 7-{N-[4-(2-tetrahydropyranyloxy)nonyl]acetamido}heptanoate as a residual oil, yield 66.7 g.

Step B. Preparation of 7-[N-(4-hydroxynonyl)-acetamido]heptanoic acid

A solution is prepared from ethyl 7-{N-[4-(2-tetrahydropyranyloxy)nonyl]acetamido}heptanoate (4.5 g., 0.01 mole), ethanol (50 ml.) and 4 drops of concentrated hydrochloric acid, and kept at ambient temperature for 4.5 hours. Then to the reaction mixture is added a solution of sodium hydroxide (0.72 g., 0.018 mole) in water (8 ml.) and the mixture is kept at ambient temperature for an additional twenty hours. Most of the ethanol is removed by evaportion in vacuo and the resulting solution is diluted with water (100 ml.). This solution is extracted, once with ether, then acidified with hydrochloric acid. The oil that separates is extracted into ether, the ethereal extract is dried over sodium sulfate, then the solvent is removed under vacuum to give 7-[N-(4-hydroxynonyl)acetamido]heptanoic acid as a yellow oil; pmr (CDCl$_3$) δ 0.93 (3H,m CH$_3$), 2.10 (3H,s CH$_3$CO), 3.38 (4H,m NCH), 7.03 (2H,s COOH, OH).

Analysis calculated for C$_{18}$H$_{35}$NO$_4$: C, 65.61; H, 10.71; N, 4.25. Found: C, 65.91; H, 10.87; N, 4.71.

EXAMPLE 2

Preparation of 7-[N-(4-Hydroxynonyl)acetamido]heptanoic acid

Step A. Preparation of Ethyl 7-acetamidoheptanoate

7-Aminoheptanoic acid (24 g., 0.165 mole), acetic anhydride (40.8 g., 0.40 mole), and water (60 ml.) are stirred at room temperature for 3 hours. The volatile materials are removed by distillation in vacuo. The liquid residue is dissolved in a mixture of benzene (100 ml.), ethanol (40 ml.), and concentrated sulfuric acid (1 ml.). The solution is refluxed for 24 hours while the water that is produced is continuously removed from the reaction by means of a Dean-Stark apparatus.

The reaction mixture is cooled, poured into water (400 ml.) and the pH adjusted to 10 by the addition of aqueous sodium carbonate. The mixture is extracted with ether and the organic layer dried over anhydrous magnesium sulfate. Distillation gives ethyl 7-acetamidoheptanoate, b.p. 131°–136° C. at 0.05 mm. mercury pressure. Analysis calculated for C$_{11}$H$_{21}$NO$_3$: C, 61.36; H, 9.83; N, 6.51. Found: C, 60.93; H, 9.89; N, 6.31.

Step B. Preparation of Ethyl 7-[N-(4-acetoxynonyl)acetamido]heptanoate

The preparation of this compound is accomplished by essentially the same method as described in Example 1, Step A, except that the N-[4-(2-tetrahydropyranyloxy)nonyl]-acetamide of Example 1, Step A is replaced by an equimolar quantity of ethyl 7-acetamidoheptanoate and the ethyl 7-bromoheptanoate is replaced by an equimolar quantity of 1-chloro-4-acetoxynonane (Example A, Step 4). Purification of the product by column chromatography on silica gel gives ethyl 7-[N-(4-acetoxynonyl)acetamido]heptanoate.

Analysis calculated for C$_{22}$H$_{41}$NO$_5$: C, 66.14; H, 10.34; N, 3.51. Found: C, 66.27; H, 10.52; N, 3.14.

Step C. Preparation of 7-[N-(4-Hydroxynonyl)acetamido]heptanoic acid

The preparation of this compound is carried out essentially by the method described for Example 1, Step B except that the ethyl 7-{N-[4-(2-tetrahydropyranyloxy)-nonyl]acetamido}heptanoate of Example 1, Step B is replaced by an equimolar quantity of ethyl 7-[N-(4-acetoxynonyl)-acetamido]heptanoate; and omitting the acid treatment, there is obtained the subject compound.

EXAMPLE 3

Preparation of 7-[N-(4-Hydroxynonyl)formamido]heptanoic acid

The synthesis of this compound is carried out as described in Example 2 except that, in Step A, the acetic anhydride is replaced by an equimolar amount of formic acetic anhydride. The product of Step A is thus ethyl 7-formamidoheptanoate. Subsequent steps yield: ethyl 7-[N-(4-acetoxynonyl)formamido]heptanoate (B); and 7-[N-(4-hydroxynonyl)formamido]heptanoic acid (C).

EXAMPLE 4

Preparation of 7-[N-(4-Hydroxynonyl)propionamido]heptanoic acid

The synthesis of this compound is carried out as described in Example 2 except that, in Step A, the acetic anhydride is replaced by an equimolar amount of propionic anhydride. The product of Step A is ethyl 7-propionamidoheptanoate. Subsequent steps yield: ethyl 7-[N-(4-acetoxynonyl)propionamido]heptanoate (B); and 7-[N-(4-hydroxynonyl)propionamido]heptanoic acid (C).

EXAMPLE 5

Preparation of 7-[N-(4-Hydroxynonyl)acrylamido]heptanoic acid

The synthesis of this compound is carried out as described in Example 2 except that, in Step A, the acetic anhydride is replaced by a large excess of acryloyl chloride (used as the solvent) and the water is omitted. The product of Step A is ethyl 7-acrylamidoheptanoate. Subsequent steps yield: ethyl 7-[N-(4-acetoxynonyl)-acrylamido]heptanoate (B); and 7-[N-(4-hydroxynonyl)acrylamido]heptanoic acid (C).

EXAMPLE 6

Preparation of 7-[N-(4-Hydroxynonyl)-2-hydroxyacetamido]-heptanoic acid

The synthesis of this compound is carried out as described in Example 2 except that, in Step A, the acetic anhydride is replaced by an equimolar amount of chloroacetic anhydride. The product of Step A is ethyl 7-(2-chloroacetamido)heptanoate. Subsequent steps yield: ethyl 7-[N-(4-acetoxynonyl)-2-chloroacetamido] heptanoate (B); and 7-[N-(4-hydroxynonyl-2-hydroxyacetamido]-heptanoic acid (C); (the basic hydrolytic conditions cause the replacement of the chlorine atom by hydroxy in this step).

EXAMPLE 7

Preparation of 7-[(4-Hydroxynonyl)trifluoroacetamido]-heptanoic acid

The synthesis of this compound is carried out as described in Example 2 except that, in Step A, the acetic anhydride is replaced by an excess of trifluoroacetic anhydride and the water is omitted. The product of Step A is ethyl 7-trifluoroacetamidoheptanoate. Subsequent steps yield: ethyl 7-[N-(4-acetoxynonyl)-trifluoroacetamido]heptanoate (B); and 7-[N-(4-hydroxynonyl)-trifluoroacetamido]heptanoic acid (C).

EXAMPLE 8

Preparation of 7-[N-(4-hydroxynonyl)acetamido]-2-methyl-heptanoic acid

The synthesis of this compound is carried out as described in Exanple 1 except that, in Step A, the ethyl 7-bromoheptanoate is replaced by an equimolar amount of methyl 7-bromo-2-methylheptanoate (Example L, Step 4). The product of Step A is methyl 7-{N-[4-(2-tetrahydropyranyloxy)nonyl]acetamido}-2-methylheptanoate. The subsequent step yields 7-[N-(4-hydroxynonyl)acetamido]-2-methylheptanoic acid (B).

EXAMPLE 9

Preparation of 7-[N-(4-Hydroxynonyl)acetamido]-3-methylheptanoic acid

The synthesis of this compound is carried out as described in Example 1 except that, in Step A, the ethyl 7-bromoheptanoate is replaced by an equimolar amount of methyl 3-methyl-7-iodoheptanoate. The product of Step A is methyl 7-{N-[4-(2-tetrahydropyranyloxy)nonyl]acetamido}-3-methylheptanoate. The subsequent step yields 7-[N-(4-hydroxynonyl)acetamido]-3-methylheptanoic acid (B).

EXAMPLE 10

Preparation of 7-[N-(4-Hydroxynonyl)acetamido]-2,2-dimethylheptanoic acid

The synthesis of this compound is carried out as described in Example 1 except that, in Step A, the ethyl 7-bromoheptanoate is replaced by an equimolar amount of methyl 2,2-dimethyl-7-iodoheptanoate. The product of Step A is methyl 7-{N-[4-(2-tetrahydropyranyloxy)nonyl]-acetamido}-2,2-dimethylheptanoate. The subsequent step yields 7-[N-(4-hydroxynonyl)acetamido]-2,2-dimethylheptanoic acid (B).

EXAMPLE 11

Preparation of 7-[N-(4-Hydroxynonyl)acetamido]-3,3-dimethylheptanoic acid

The synthesis of this compound is carried out as described in Example 1 except that, in Step A, the ethyl 7-bromoheptanoate is replaced by an equimolar amount of methyl 3,3-dimethyl-7-iodoheptanoate. The product of Step A is methyl 7-{N-[4-(2-tetrahydropyranyloxy)nonyl]-acetamido}-3,3-dimethylheptanoate. The subsequent step yields 7- [N-(4-hydroxynonyl)acetamido]-3,3-dimethylheptanoic acid (B).

EXAMPLE 12

Preparation of 4-[N-(4-Hydroxynonyl)acetamido]butoxyacetic acid

The synthesis of this compound is carried out as described in Example 1 except that, in Step A, the ethyl 7-bromoheptanoate is replaced by an equimolar amount of ethyl 4-bromobutoxyacetic (Example M). The product of Step A is ethyl 4-{N-[4-(2-tetrahydropyranyloxy)nonyl]-acetamido}butoxyacetate. The subsequent step yields 4-[N-(4-hydroxynonyl)acetamido]butoxyacetic acid (B).

EXAMPLE 13

Preparation of 7-[N-(4-Hydroxy-8-methylnonyl)acetamido]-heptanoic acid

The synthesis of this compound is carried out as described in Example 2 except that, in Step B, the 1-chloro-4-acetoxynonane is replaced by an equimolar amount of 1-chloro-4-acetoxy-8-methylnonane (Example B, Step 3). The product of Step B is ethyl 7-[N-(4-acetoxy-8-methyl-nonyl)acetamido]heptanoate. The subsequent step yields 7-[N-(4-hydroxy-8-methylnonyl)acetamido]heptanoic acid (C).

EXAMPLE 14

Preparation of 7-[N-(4-Hydroxyundecanyl)acetamido]heptanoic acid

The synthesis of this compound is carried out as described in Example 2 except that, in Step B, the 1-chloro-4-acetoxynonane is replaced by an equimolar amount of 1-chloro-4-acetoxyundecane (Example C, Step 3). The product of Step B is ethyl 7-[N-(4-acetoxyundecanyl)-acetamido]heptanoate. The subsequent step yields 7-[N-(4-hydroxyundecanyl)acetamido]heptanoic acid (C).

EXAMPLE 15

Preparation of
7-[N-(4-Hydroxy-8,8-dimethylnonyl)acetamido]-heptanoic acid

The synthesis of this compound is carried out as described in Example 2 except that, in Step B, the 1-chloro-4-acetoxynonane is replaced by an equimolar amount of 1-chloro-4-acetoxy-8,8-dimethylnonane (Example D). The product of Step B is ethyl 7-[N-(4-acetoxy-8,8-dimethylnonyl)acetamido]heptanoate. The subsequent step yields 7-[N-(4-hydroxy-8,8-dimethylnonyl)acetamido]heptanoic acid (C).

EXAMPLE 16

Preparation of
7-[N-(4-Hydroxy-9,9,9-trifluorononyl)-acetamido]-heptanoic acid

The synthesis of this compound is carried out as described in Example 2 except that, in Step B, the 1-chloro-4-acetoxynonane is replaced by an equimolar amount of 1-chloro-4-acetoxy-9,9,9-trifluorononane (Example E). The product of Step B is ethyl 7-[N-(4-acetoxy-9,9,9-trifluorononyl)acetamido]heptanoate. The subsequent step yields 7-[N-(4-hydroxy-9,9,9-trifluorononyl)acetamido]-heptanoic acid (C).

EXAMPLE 17

Preparation of
7-[N-(4-Hydroxy-8-nonenyl)acetamido]-heptanoic acid

The synthesis of this compound is -nonenyl-)acetamido]out as described in Example 2 except that, in Step B, the 1-chloro-4-acetoxynonane is replaced by an equimolar amount of 1-chloro-4-acetoxy-8-nonene. The product of Step B is ethyl 7-[N-(4-acetoxy-8-nonenyl)acetamido]-heptanoate. The subsequent step yields 7-[N-(4-hydroxy-8-nonenyl)acetamido]heptanoic acid (C).

EXAMPLE 18

Preparation of
7-[N-(4-Hydroxy-(E)-2-nonenyl)acetamido,9-heptanoic acid

The synthesis of this compound is carried out as described in Example 2 except that, in Step B, the 1-chloro-4-acetoxynonane is replaced by an equimolar amount of 1-bromo-4-acetoxy-2-nonene (Example H). The product of Step B is ethyl 7-[N-(4-acetoxy-(E)-2-nonenyl)acetamido]-heptanoate. The subsequent step yields 7-[N-(4-hydroxy-2-noneneyl)acetamido]heptanoic acid (C).

EXAMPLE 19

Preparation of
7-[N-(4-Hydroxy-2-nonynyl)acetamido]-heptanoic acid

The synthesis of this compound is carried out as described in Example 2 except that, in Step B, the 1-chloro-4-acetoxynonane is replaced by an equimolar amount of 1-bromo-4-acetoxy-2-nonyne (Example I, Step 3). The product of Step B is ethyl 7-[N-(4-acetoxy-2-nonynyl)acetamido]heptanoate. The subsequent step yields 7-[N-(4-hydroxy-2-nonynyl)acetamido]heptanoic acid (C).

EXAMPLE 20

Preparation of
7-[N-(4(R)-Hydroxynonyl)acetamido]heptanoic acid

The snthesis of this compound is carried out as described in Example 2 except that, in Step B, the 1-chloro-4-acetoxynonane is replaced by an equimolar amount of 1-bromo-4(R)-acetoxy-2-nonyne (Example J). The product of Step B is ethyl 7-[N-(4(R)-acetoxy-2-nonynyl)-acetamido]heptanoate. The subsequent step yields 7-[N-(4(R)-hydroxy-2-nonynyl)acetamido]heptanoic acid (C). The product of Step C is hydrogenated over a platinum on charcoal catalyst to afford 7-[N-(4(R)-hydroxynonyl)-acetamido]heptanoic acid (D).

EXAMPLE 21

Preparation of
7-[N-(4(S)-Hydroxynonyl)acetamido]heptanoic acid

The synthesis of this compound is carried out as described in Example 2 except that, in Step B, the 1-chloro-4-acetoxynonane is replaced by an equimolar amount of 1-bromo-4(S)-acetoxy-2-nonyne (Example K). The product of Step B is ethyl 7-[N-(4(S)-acetoxy-2-nonynyl)acetamido]-heptanoate. The subsequent step yields 7-[N-(4(S)-hydroxy-2-nonynyl)acetamido]heptanoic acid (C). The product of Step C is hydrogenated over a platinum on charcoal catalyst to afford 7-[N-(4(S)-hydroxynonyl)acetamido]-heptanoic acid (D).

EXAMPLE 22

Preparation of
7-[N-(4-Hydroxy-5,5-dimethylnonyl)acetamido]-heptanoic acid

The synthesis of this compound is carried out as described in Example 2 except that, in Step B, the 1-chloro-4-acetoxynonane is replaced by an equimolar amount of 1-chloro-4-acetoxy-5,5-dimethylnonane (Example G, Step 3). The product in Step B is ethyl 7-[N-(4-acetoxy-5,5-dimethylnonyl)acetamido]heptanoate. The subsequent step yields 7-[N-(4-hydroxy-5,5-dimethylnonyl)acetamido]-heptanoic acid (C).

EXAMPLE 23

Preparation of
7-[N-(4-Acetoxynonyl)acetamido]heptanoic acid

A mixture of 7-[N-(4-hydroxynonyl)acetamido]-heptanoic acid (9.8 g., 0.03 mole) (Example 1, Step C) and acetic anhydride (6.1 g., 0.06 mole) is heated at 60° C. for 18 hours. The mixture is cooled and taken up in 80 ml. of ethyl ether. The solution is extracted with and ice-cold solution of 8 g. of sodium hydroxide in 150 ml. of water. The basic solution is separated and acidified with concentrated hydrochloric acid. The crude product that separates is extracted into ether, washed with water and dried over sodium sulfate. The ether is evaporated and the residual oil is purified by chromatoraphy on slica gel using 2% methanol in chloroform as the eluting solvent. There is obtained 7-[N-(4-acetoxynonyl)acetamido]heptanoic acid as a viscous oil.

By substituting for the acetic anhydride used in Example 21, an equivalent amount of propionic anhydride, butyric anhydride, isobutyric anhydride, valeric anhydride, or pivalic anhydride and conducting the reaction as described in Example 21, there is obtained 7-[N-(4-propionyloxynonyl)acetamido]heptanoic acid, 7-[N-(4-butyryloxynonyl)acetamido]heptanoic acid, 7-[N-(4-isobutyryloxynonyl)acetamido]heptanoic acid, 7-[N-(4-valeryloxynonyl)-acetamido]heptanoic acid, and 7-[N-(4-pivaloyloxynonyl)-acetamido]heptanoic acid, respectively.

EXAMPLE 24

Preparation of Methyl 7-[N-(4-Hydroxynonyl)acetamido]-heptanoate

A solution of diazomethane (approx. 2.5 g., 0.06 mole) in ether (100 ml.) is mixed with a solution of 7-[N-(4-hydroxynonyl)acetamido]heptanoic acid (9.8 g., 0.03 mole) (Example 1, Step C) in ether (50 ml.). The resulting solution is allowed to stand 4 hours at room temperature. Acetic acid is then added to destroy the excess diazomethane and the solution is washed with dilute sodium bicarbonate solution and water and dried over sodium sulfate. Evaporation of volatile materials at reduced pressure yields methyl 7-[N-(4-hydroxynonyl)acetamido]-heptanoate as a viscous oil.

EXAMPLE 25

Preparation of Decyl 7-[N-(4-Hydroxynonyl)acetamido]-heptanoate

Using the method of Example 23 but substituting an ether solution of 1-diazodecane for the ether solution of diazomethane, there is obtained decyl 7-[N-(4-hydroxynonyl)acetamido]heptanoate, as a viscous oil.

EXAMPLE 26

Preparation of N-[(2-Dimethylamino)ethyl]-7-[N-(4-hydroxynonyl)acetamido]heptanamide A solution of 7-[N-(4-hydroxynonyl)acetamido]-heptanoic acid (3.28 g., 10 millimoles) (Example 1, Step C), triethylamine (1.74 ml., 12.5 millimoles) and distilled water (18 ml.) in acetonitrile (100 ml.) is treated with N-t-butyl-5-methyl-isoxazolium perchlorate (3.0 g., 12.5 millimoles). The resulting solution is evaporated in vacuo at 20°–25° C. over 4 hours providing a tacky residue which is triturated with water (150 ml.) at 0°–5° C. for 15 minutes. After decanting the aqueous phase, the oily residue is dissolved in benzene-ether [(1:1), 200 ml.]. The organic extract is dried over sodium sulfate, then evaporated in vacuo providing the desired "active ester".

A solution of 2-dimethylaminoethylamine (0.88 g., 10 millimoles) in acetonitrile (25 ml.) is added to a solution of the "active ester" in acetonitrile (25 ml.) and the solution is stirred at 25° C. for 17 hours. The solvent is removed in vacuo, the residual oil is partitioned between ether (200 ml.) and water (200 ml.). The ether layer is extracted with 5% hydrochloric acid (2 × 50 ml.). The aqueous acid phase is made basic with aqueous sodium carbonate then extracted with ether. The ether extract is washed with brine solution (100 ml.), dried over sodium sulfate, evaporated in vacuo leaving the N-[(2-dimethylamino)ethyl]-7-[N-(4-hydroxynonyl)acetamido]heptanamide as a viscous oil.

What is claimed is:

1. The compound of the formula:

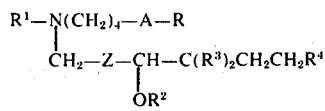

wherein A is ethylene, trimethylene, α-methylethylene, β-methylethylene, α,α-dimethylethylene, or β,β-dimethylethylene;

$R^1$ is formyl, acetyl, propionyl, acryloyl, hydroxyacetyl, or trifluoroacetyl;

Z is ethylene, vinylene, or ethynylene;

$R^2$ is hydrogen or loweralkanoyl;

$R^3$ is hydrogen or methyl;

$R^4$ is hydrogen, loweralkyl, vinyl, or 2,2,2-trifluoroethyl; and

R is carboxy, a carboxy salt having the formula:

wherein Me is a pharmaceutically acceptable cation derived from a metal or an amine, or derivatized carboxy having the formula:

wherein $R^5$ is alkyl having 1–10 carbon atoms.

2. The compound of claim 1 wherein R is carboxy or a pharmaceutically acceptable salt.

3. The compound of claim 2 which has the formula:

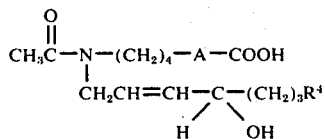

wherein

A is ethylene, trimethylene, α-methylethylene, β-methylethylene, α,α-dimethylethylene, or β,β-dimethylethylene; and $R^4$ is hydrogen, loweralkyl of 1–4 carbon atoms, or 2,2,2-trifluoroethyl.

4. The compound of claim 3 wherein A is ethylene and $R^4$ is ethyl.

5. The compound of claim 2 which has the formula:

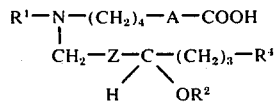

in which $R^1$ is formyl, acetyl, propionyl, acryloyl, hydroxyacetyl, or trifluoroacetyl;

A is ethylene, trimethylene, α-methylethylene, β-methylethylene, α,α-dimethylethylene, or β,β-dimethylethylene;

Z is ethylene, vinylene, or ethynylene;

$R^4$ is hydrogen, loweralkyl, vinyl, or 2,2,2-trifluoroethyl; and $R^2$ is loweralkanoyl or hydrogen.

6. The compound of claim 5 wherein A and Z are ethylene, $R^1$ is acetyl, $R^2$ is formyl, and $R^4$ is ethyl.

7. The compound of claim 5 wherein A and Z are ethylene, $R^1$ is acetyl, $R^4$ is ethyl, and $R^2$ is acetyl.

8. The compound of claim 2 which has the formula:

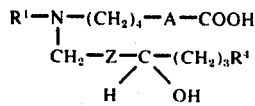

wherein
- $R^1$ is formyl, acetyl, propionyl, acryloyl, hydroxyacetyl, or trifluoroacetyl;
- A is ethylene, trimethylene, α-methylethylene, β-methylethylene, α,α-dimethylethylene, or β,β-dimethylethylene;
- Z is ethylene, vinylene or ethynylene; and
- $R^4$ is hydrogen, loweralkyl, vinyl, or 2,2,2-trifluoroethyl.

9. The compound of claim 8 wherein $R^1$ is acetyl or propionyl.

10. The compound of claim 9 wherein A and Z are ethylene, $R^1$ is acryloyl and $R^4$ is ethyl.

11. The compound of claim 9 wherein A and Z are ethylene, $R^1$ is acetyl and $R^4$ is 2,2,2-trifluoroethyl.

12. The compound of claim 9 wherein A and Z are ethylene, $R^1$ is acetyl and $R^4$ is vinyl.

13. The compound of claim 9 wherein $R^4$ is straight chain loweralkyl having 2–5 carbon atoms.

14. The compound of claim 13 wherein A and Z are ethylene, $R^1$ is acetyl, and $R^4$ is butyl.

15. The compound of claim 13 wherein A and Z are ethylene, $R^1$ is acetyl and $R^4$ is tert.-butyl.

16. The compound of claim 9 wherein Z and A are ethylene, and $R^4$ is ethyl.

17. 7-[N-(4-Hydroxynonyl)propionamido]heptanoic acid, the compound of claim 16 wherein $R^1$ is propionyl.

18. 7-[N-(4-Hydroxynonyl)acetamido]heptanoic acid, the compound of claim 16 wherein $R^1$ is acetyl.

19. The compound of claim 18 wherein $R^1$ is acetyl and the carbon atom bearing the hydroxy group is in the R configuration.

20. The compound of claim 18 wherein $R^1$ is acetyl and the carbon atom bearing the hydroxy group is in the S configuration.

* * * * *